United States Patent [19]
Georgeson et al.

[11] Patent Number: 5,902,935
[45] Date of Patent: May 11, 1999

[54] NONDESTRUCTIVE EVALUATION OF COMPOSITE BONDS, ESPECIALLY THERMOPLASTIC INDUCTION WELDS

[76] Inventors: Gary E. Georgeson; Larry E. Dolan, both of The Boeing Company, P.O. Box 3707, M/S 13-08, Seattle, Wash. 98124-2207

[21] Appl. No.: 08/907,533

[22] Filed: Aug. 8, 1997

Related U.S. Application Data

[XX .
[60] Provisional application No. 60/025,343, Sep. 3, 1996.

[51] Int. Cl.⁶ .................................................. G01N 29/04
[52] U.S. Cl. ................................ 73/801; 73/827; 73/850
[58] Field of Search ............................. 73/801, 629, 632, 73/587, 588, 600, 827, 850

[56] References Cited

U.S. PATENT DOCUMENTS

| | | |
|---|---|---|
| 2,241,312 | 5/1941 | Luty . |
| 2,273,423 | 2/1942 | Somes . |
| 2,372,920 | 4/1945 | Blessing . |
| 2,378,801 | 6/1945 | Sidell et al. . |
| 2,423,922 | 7/1947 | Arndt, Jr. . |
| 2,589,777 | 3/1952 | Collins . |
| 2,739,829 | 3/1956 | Pedlow et al. . |
| 2,761,941 | 9/1956 | Ardichvili . |
| 2,898,435 | 8/1959 | Crafts . |
| 2,903,886 | 2/1959 | Renaut . |
| 3,101,403 | 8/1963 | Lewis et al. . |
| 3,183,460 | 5/1965 | Bennon . |
| 3,288,979 | 11/1966 | Mills et al. . |
| 3,395,261 | 7/1968 | Leatherman et al. . |
| 3,431,379 | 3/1969 | Yrene . |
| 3,450,856 | 6/1969 | Buck et al. . |
| 3,492,453 | 1/1970 | Hurst . |
| 3,507,735 | 4/1970 | Chisholm . |
| 3,574,031 | 4/1971 | Heller, Jr. et al. . |
| 3,845,268 | 10/1974 | Sindt . |
| 3,864,186 | 2/1975 | Balla . |
| 3,941,643 | 3/1976 | Balla . |

(List continued on next page.)

FOREIGN PATENT DOCUMENTS

| | | |
|---|---|---|
| 0 461 979 B1 | 4/1994 | European Pat. Off. . |
| 54-25542 | 2/1979 | Japan . |

OTHER PUBLICATIONS

J. Giachino, Welding Skills and Practices, Am. Tech. Soc., Chicago, IL (1960,1965,1967,1971,1976) 393–401.

Biggiero et al., *Ultrasonic Scanning and Spectrum Analysis for Inspection of Bond Efficiency of Metal–to Metal Structural Adhesive Joints*, NDT International Apr. 1983, pp. 67–73.

*Primary Examiner*—Max H. Noori
*Attorney, Agent, or Firm*—John C. Hammar

[57] ABSTRACT

Thermoplastic welding is an emerging technology targeted at significantly reducing the manufacturing cost of aerospace structure by eliminating fasteners and the touch labor associated with fasteners to prepare, install, and inspect the assemblies. Quality welds are highly dependent upon achieving appropriate temperatures everywhere along the bond line. The present invention is a system that evaluates the quality of the welds involving inputting an EM pulse to the embedded susceptor and listening to the acoustic response that the pulse generates to determine weld quality from the sound.

10 Claims, 7 Drawing Sheets

U.S. PATENT DOCUMENTS

| | | |
|---|---|---|
| 3,946,349 | 3/1976 | Haldeman, III . |
| 3,996,402 | 12/1976 | Sindt . |
| 4,005,302 | 1/1977 | Graf et al. . |
| 4,029,837 | 6/1977 | Leatherman . |
| 4,029,926 | 6/1977 | Austin . |
| 4,091,254 | 5/1978 | Struve . |
| 4,100,809 | 7/1978 | Bobrov et al. ............................ 73/638 |
| 4,120,712 | 10/1978 | Sindt . |
| 4,180,717 | 12/1979 | Lenk et al. . |
| 4,187,411 | 2/1980 | Bryce et al. ............................ 73/627 |
| 4,287,776 | 9/1981 | Ensminger . |
| 4,288,673 | 9/1981 | Ishibashi . |
| 4,296,295 | 10/1981 | Kiuchi . |
| 4,304,975 | 12/1981 | Lenk et al. . |
| 4,313,777 | 2/1982 | Buckley et al. . |
| 4,343,982 | 8/1982 | Schwartz et al. . |
| 4,355,222 | 10/1982 | Geithman et al. . |
| 4,382,113 | 5/1983 | Schwartz et al. . |
| 4,416,713 | 11/1983 | Brooks . |
| 4,421,588 | 12/1983 | Davies . |
| 4,445,951 | 5/1984 | Lind et al. . |
| 4,521,659 | 6/1985 | Buckley et al. . |
| 4,653,396 | 3/1987 | Wennerberg . |
| 4,671,470 | 6/1987 | Jonas . |
| 4,673,450 | 6/1987 | Burke . |
| 4,768,433 | 9/1988 | Boissevain . |
| 4,791,260 | 12/1988 | Waldman . |
| 4,822,972 | 4/1989 | Sugioka et al. . |
| 4,897,518 | 1/1990 | Mucha et al. . |
| 4,904,972 | 2/1990 | Mori et al. . |
| 4,919,759 | 4/1990 | Ilmarinen et al. . |
| 4,944,185 | 7/1990 | Clark, Jr. et al. . |
| 4,947,464 | 8/1990 | Mori et al. . |
| 4,978,825 | 12/1990 | Schmidt et al. . |
| 5,001,319 | 3/1991 | Holmstrom . |
| 5,047,605 | 9/1991 | Ogden . |
| 5,074,019 | 12/1991 | Link . |
| 5,079,817 | 1/1992 | Anstotz et al. . |
| 5,101,086 | 3/1992 | Dion et al. . |
| 5,101,663 | 4/1992 | Narita et al. . |
| 5,170,666 | 12/1992 | Larsen . |
| 5,179,860 | 1/1993 | Tsuboi . |
| 5,199,791 | 4/1993 | Kasanami et al. . |
| 5,240,542 | 8/1993 | Miller et al. . |
| 5,248,864 | 9/1993 | Kodokian . |
| 5,250,776 | 10/1993 | Pfaffmann . |
| 5,283,409 | 2/1994 | Brendel et al. . |
| 5,303,590 | 4/1994 | Modderman et al. . |
| 5,313,034 | 5/1994 | Grimm et al. . |
| 5,313,037 | 5/1994 | Hansen et al. . |
| 5,340,428 | 8/1994 | Kodokian . |
| 5,351,544 | 10/1994 | Endo et al. . |
| 5,408,881 | 4/1995 | Piche et al. . |
| 5,486,684 | 1/1996 | Peterson et al. ........................ 219/633 |
| 5,573,613 | 11/1996 | Lunden .................................... 219/633 |
| 5,589,635 | 12/1996 | Baudrillard et al. . |

NONDESTRUCTIVE EVALUATION OF COMPOSITE BONDS, ESPECIALLY THERMOPLASTIC INDUCTION WELDS

REFERENCE TO RELATED APPLICATION

The present application claims the benefit of U.S. Provisional Application 60/025,343, filed Sep. 3, 1996.

TECHNICAL FIELD

The present invention is a nondestructive method for evaluating the quality and integrity of a thermoplastic weld having an embedded susceptor. The method uses an impulse coil to vibrate the susceptor and an acoustic sensor to listen to the vibration to assess the weld quality, generally through analysis of the return signal in the frequency domain.

BACKGROUND ART

Composite materials lend themselves to bonded structures better than to fastened ones. Bonded composites have received limited use in critical aerospace structures, however, because the bonds can vary in strength or stiffness even if they have no discrete bond line defects (disbonds, porosity, voids, cracking, etc.). Traditional nondestructive inspection methods rely upon quantifying these defects to predict the flightworthiness of the structure, but are unable to ascertain the cohesiveness of the bond at any location if defects are absent. Nondestructive identification of low strength bonds and regions of "kissing unbonds" (bonds of near zero strength) remains a significant goal solved only in a few specific bonded applications where the results of shear or tensile tests have been correlated to a particular NDE signal feature. Modified pulse-echo ultrasonic testing (UT) has been successful in finding the discrete defects (voids, delaminations, porosity), but not "kissing unbonds" and low strength bonds. Infrared thermography, shearography, eddy current, and various high and low frequency ultrasonic methods have also been unsuccessful in discerning bond quality in thermoplastic welds.

The present invention provides a nondestructive method for testing bond quality using an electromagnetic (EM) pulse to induce vibrations in the embedded susceptor and an acoustic receiver to listen to and to record the induced vibrations. Analysis of the received vibration signal discriminates bond quality.

SUMMARY OF THE INVENTION

The present invention inspects bond lines that contain conductive material, especially those formed using a copper mesh susceptor, using high energy electromagnetic pulsing with acoustic receiving in a single inspection head to produce a unique evaluation technique. The inspection head contacts the outer skin of the structure whose bond is being evaluated, and contains a pancake type copper coil containing windings with rectangular cross sections designed to effectively couple to the susceptor. The closing of a switch releases a charge built up in a capacitor bank, which creates a high energy pulse in the coil. The electromagnetic field produced by the current pulse couples to the susceptor, opposes the driving magnetic field of the coil, and creates a force on the susceptor. With the help of a finite element code for electromagnetic interactions, we have been able to model the test setup and predict the forces on the susceptor. For the EM pulse produced by the discharge of a capacitor bank (proportional to the voltage of the coil), the normal stresses induced in the susceptor are shown in FIG. 3. The frequency of the stress peaks in the time domain is twice that of the voltage peaks at the coil, because a change (positive or negative) occurs on both sides of each peak.

The stresses incite vibrational modes in the susceptor and surrounding composite, creating an acoustic wave that we receive and record with an electromagnetically shielded acoustic-emission (AE) transducer at the center or around the outside of the coil (FIG. 4). While the size of the signal will depend upon the size of the incoming pulse, the susceptor conductivity, and the depth of the bond line, frequency-related features of the signal can be correlated to bond quality. We have demonstrated experimentally that a susceptor that is not fully bonded to the surrounding substructure will produce low frequency modes that are absent in a well bonded structure. The difference in the frequency response produced from a good bond and a poor bond is shown in FIGS. 5 and 6, respectively. FIGS. 5 & 6 plot Fourier transforms from the time domain to the frequency domain of the ultrasonic signal received at the AE transducer.

Bonds on both sides of the susceptor can be separately examined. These bonds experience both tensile and compressive stress when the susceptor vibrates. As the vibration occurs, the bond above the susceptor will be under tension as the bond below is under compression, and visa versa. We measure the response of the bond to a given induced stress level, permitting a type of in-situ proof-testing of the bond quality. "Kissing unbonds" or low strength bonds can be identified with lower energy pulses.

Some radomes contain conductive layers (the FSS layers), which may be inspected with this device. In addition, a conductive layer can be added to adhesive bond lines to produce an inspectable bonded structure from an otherwise uninspectable one.

DETAILED DESCRIPTION OF A PREFERRED EMBODIMENT

Figure 1:
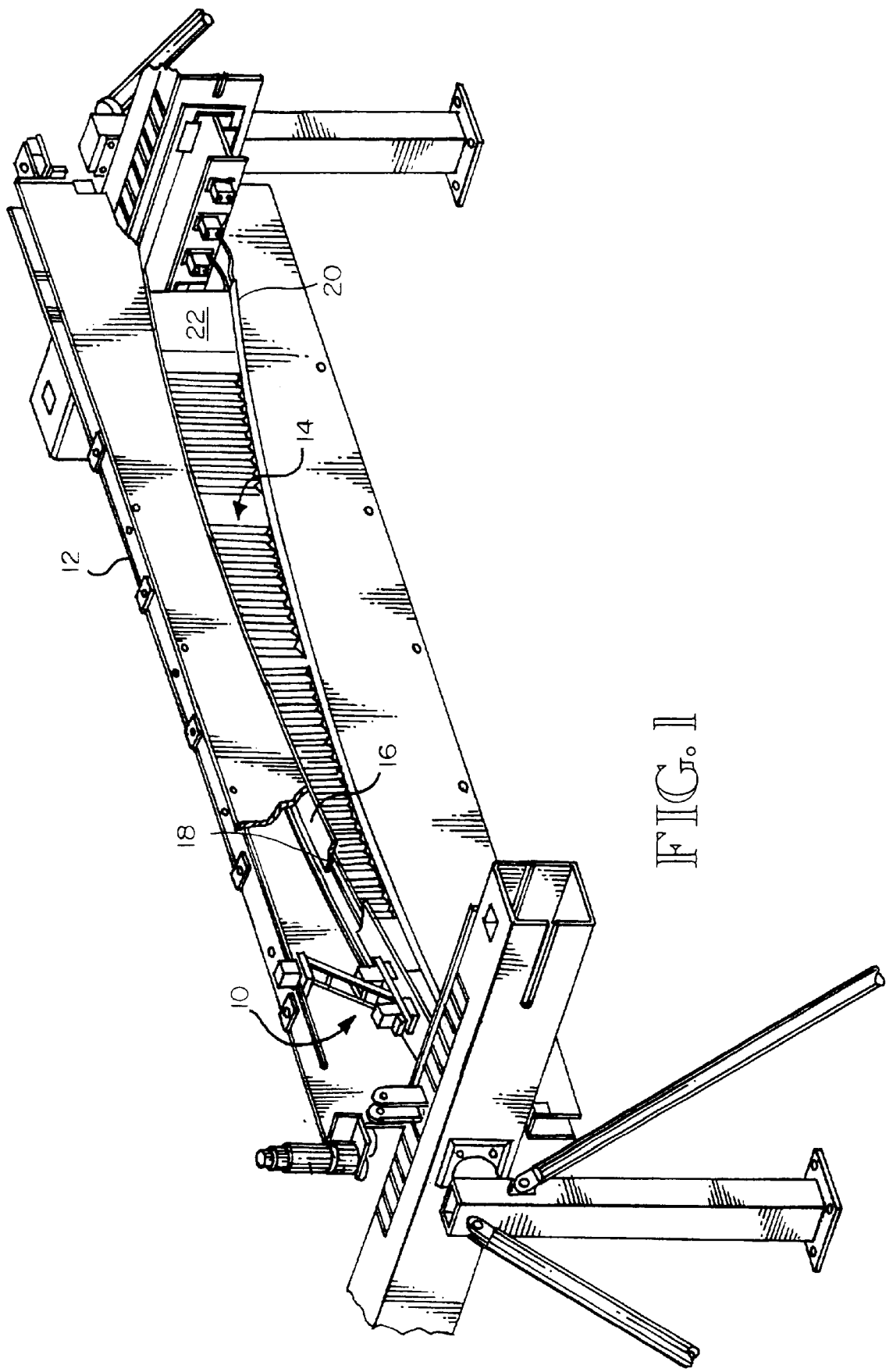
FIG. 1 is a perspective view of a moving coil thermoplastic welding apparatus.

First, we will describe a typical thermoplastic welding operation, since these are the bonds of principle interest for nondestructive evaluation in accordance with the present invention. Then, we will describe the nondestructive evaluation system (NDE) of the present invention for assessing bond quality.

For purposes of this description, "laminate" means a fiber-reinforced organic resin matrix composite having a plurality of plies of prepreg or its equivalent consolidated together and cured, as appropriate. The laminates are prefabricated by any appropriate means including automatic or hand tape lay up or tow fiber placement with autoclave consolidation and cure; resin transfer molding (RTM); SCRIMP; or the like. Generally, the organic matrix resin is a thermoplastic, especially PEK, PEEK, PEKK, ULTEM polyimide, or KIII. In the welding operation, resin in the laminates as well as resin in the susceptor melts, intermixes, and fuses to form the weld. The laminate might also be a thermoset in which case the welding process actually forms a hot melt adhesive bond rather than a weld. We prefer welding, but recognize application of our NDE/NDI process to assess the strength and quality of adhesive bonds.

In a thermoplastic laminate, the reinforcing fiber typically is carbon fiber in continuous or chopped form, and generally as tow or woven fabric. While other fibers can be used, modern aerospace requirements most often dictate carbon fibers for their strength and durability, and we prefer them. In thermosets, especially epoxy, the fibers might be graphite or fiberglass.

Thermoplastic Welding

Three major joining technologies exist for joining aerospace composite structure: mechanical fastening; adhesive bonding; and welding. Both mechanical fastening and adhesive bonding use costly, timeconsuming assembly steps that introduce excess cost into the manufacture of aerospace composite assemblies even if the parts are fabricated from components produced by an emerging, cost efficient process. Mechanical fastening requires expensive hole locating, drilling, shimming, and fastener installation, while adhesive bonding usually requires complicated surface pretreatments.

In contrast, composite welding eliminates fasteners and can join thermoplastic composite components at high speeds with minimum touch labor and little, if any, pretreatments. In our experience, the welding interlayer, called a susceptor, also can simultaneously take the place of shims required in mechanical fastening. As such, composite welding holds promise to be an affordable joining process. For "welding" thermoplastic and thermoset composite parts together, the resin that the susceptor melts functions as a hot melt adhesive. If fully realized, this thermoplastic-thermoset bonding process, in addition to true thermoplastic welding, will further reduce the cost of composite assembly.

Thermoplastic welding is a process for forming a fusion bond between the faying thermoplastic faces of two or more parts. A fusion bond is created when the thermoplastic on the surface of the two parts is heated to the melting or softening point and the two surfaces are brought into contact so that the molten thermoplastic mixes. Then, the surfaces are held in contact while the thermoplastic cools below the softening temperature to fuse the thermoplastic into the weld.

There is a significant stake in developing a successful thermoplastic welding process. Its advantages versus traditional composite joining methods are:

- reduced parts count versus fasteners
- minimal surface preparation, in most cases a simple solvent wipe to remove surface contaminants
- indefinite shelf life at room temperature
- short process cycle time, typically measured in minutes when using induction heating
- enhanced joint performance, especially hot/wet and fatigue
- permits rapid field repair of composites or other structures.
- little or no loss of bond strength after prolonged exposure to environmental influences.

The exponential decay of the strength of magnetic fields with distance from their source dictates that, in induction welding processes, the structure closest to the induction coil will be the hottest, since it experiences the strongest field. Therefore, it is difficult to obtain adequate heating at the bond line between two graphite or carbon fiber reinforced resin matrix composites relying on the susceptibility of the fibers alone as the source of heating in the assembly. For the inner plies to be hot enough to melt the resin, the outer plies closer to the induction coil and in the stronger magnetic field are too hot. The matrix resin in the entire piece of composite melts. The overheating results in porosity in the product, delamination, and, in some cases, destruction or denaturing of the resin. To avoid overheating of the outer plies and to insure adequate heating of the inner plies, a susceptor of significantly higher conductivity than the fibers is used to peak the heating selectively at the bond line of the plies when heating from one side. An electromagnetic induction coil on one side of the assembly heats a susceptor to melt and cure a thermoplastic resin (also sometimes referred to as an adhesive) to bond the elements of the assembly together. Often the current density in the susceptor is higher at the edges of the susceptor than in the center because of the nonlinearity of the coil. This problem typically occurs when using a cup core induction coil like that described in U.S. Pat. No. 5,313,037 and can result in overheating the edges of the assembly or underheating the center, either condition leading to inferior welds because of non-uniform curing. It is necessary to have an open or mesh pattern in the susceptor to allow the resin to bond between the composite elements of the assembly when the resin heats and melts. Misalignment can also result in temperature variations, producing excessive heating in isolated locations because of the induction physics. U.S. patent application Ser. No. 08/565,566 describes one mechanism for achieving proper alignment between the moving induction coil and the susceptor to reduce problems associated with excessive heating.

U.S. Pat. No. 4,673,450 describes a method to spot weld graphite fiber reinforced PEEK composites using a pair of electrodes After roughening the surfaces of the prefabricated PEEK composites in the region of the bond, Burke placed a PEEK adhesive ply along the bond line, applied a pressure of about 50–100 psi through the electrodes, and heated the embedded graphite fibers by applying a voltage in the range of 20–40 volts at 30–40 amps for approximately 5–10 seconds with the electrodes. Access to both sides of the assembly is required in this process which limits its application.

Prior art disclosing thermoplastic welding with induction heating is illustrated by U.S. Pat. Nos. 3,966,402 and 4,120,712. In these patents, the metallic susceptors are of a conventional type having a regular pattern of openings of traditional manufacture. Achieving a uniform, controllable temperature in the bond line, which is crucial to preparing a thermoplastic weld of adequate integrity to permit use of welding in aerospace primary structure, but is difficult to achieve with those conventional susceptors, as we discussed and illustrated in U.S. Pat. No. 5,500,511.

Simple as the thermoplastic welding process sounds, and as easy as it is to perform in the laboratory on small pieces, it becomes difficult to perform reliably and repeatably in a real factory on full-scale parts to build a large structure such as an airplane wing box. One difficulty is in getting the proper amount of heat to the bond line without overheating the entire structure. Another is achieving intimate contact of the faying surfaces of the two parts at the bond line during heating and cooling despite the normal imperfections in the flatness of composite parts, thermal expansion of the thermoplastic during heating to the softening or melting temperature, flow of the thermoplastic out of the bond line under pressure, and then contraction of the thermoplastic in the bond line during cooling.

a. Moving coil welding processes

In U.S. Pat. No. 5,500,511, Boeing described a tailored susceptor for approaching the desired temperature uniformity. This susceptor relied upon carefully controlling the geometry of openings in the susceptor (both their orientation and their spacing) to distribute the heat evenly. For example, using a regular array of anisotropic, diamond shaped openings with a ratio of the length (L) to the width (W) greater than 1 provided a superior weld over that achieved using a susceptor having a similar array, but one where the L/W ratio was one. By changing the length to width ratio (the aspect ratio) of the diamond-shaped openings in the susceptor, Boeing achieved a large difference in the longitudinal and transverse conductivity in the susceptor, and, thereby, tailored the current density within the susceptor. A tailored susceptor having openings with a length (L) to width (W) ratio of 2:1 has a longitudinal conductivity about four times the transverse conductivity. In addition to tailoring the shape of the openings to tailor the susceptor, Boeing altered the current density in regions near the edges by increasing the foil density (i.e., the absolute amount of metal). Increasing the foil density along the edge of the susceptor increased the conductivity along the edge and reduced the current density and the edge heating. The tailored susceptor had increased foil density by folding the susceptor to form edge strips of double thickness or by compressing openings near the edge of an otherwise uniform susceptor. Boeing found this susceptor difficult to reproduce reliably. Also, its use forced careful placement and alignment to achieve the desired effect when using the cup coil of U.S. Pat. No. 5,313,037 and the multipass welding process of U.S. Pat. No. 5,486,684, both of which we incorporate by reference.

With the cup coil, the magnetic field is strongest near the edges because the central pole creates a null at the center. Therefore, the susceptor is designed to counter the higher field at the edges by accommodating the naturally higher induced current near the edges. The high longitudinal conductivity encourages induced currents to flow longitudinally.

With the tailored susceptor or with other moving coil welding operations, achieving the proper bond line temperature requires empirical design calibration. Even then, the bond line temperature may fluctuate within a relatively wide range because of misalignment, variations in the susceptor, variations in the geometry (such as skin plies or spar curvature), or variations in coil speed or coil power. Boeing has created calibration curves (i.e., allowables data) for a specified power at a specified head speed, geometry, and material system. The allowables data must be quite extensive, and there is still no assurance that an actual run is producing a weld that corresponds to the test data. Monitoring the bond line temperature in real time to achieve uniform temperatures at the bond line has great significance to achieving process control and quality welds. Assessing the weld quality nondestructively is also essential since bonds of inadequate strength would produce catastrophe for the end product.

Boeing described a selvaged susceptor for thermoplastic welding in U.S. Pat. No. 5,508,496. That selvaged susceptor controls the current density pattern during eddy current heating by an induction coil to provide substantially uniform heating to a composite assembly and to insure the strength and integrity of the weld in the completed part. This susceptor is particularly desirable for welding ribs between prior welded spars using an asymmetric induction coil of U.S. Pat. No. 5,444,220, because that coil provides a controllable area of intense, uniform heating under the poles, a trailing region with essentially no heating, and a leading region with minor preheating. We incorporate these patents by reference.

Boeing achieved better performance (i.e., more uniform heating) in rib welding by using the selvaged susceptor having a center portion with a regular pattern of openings and solid foil edges, which it refers to as selvage edge strips. Embedding the susceptor in a thermoplastic resin makes a susceptor/resin tape that is easy to handle and to use in assembling the composite pieces prior to welding. With a selvaged susceptor, the impedance of the central portion should be anisotropic with a lower transverse impedance than the longitudinal impedance. Here, the L/W ratio of diamond shaped openings should be less than or equal to one. That is, unlike the tailored susceptor of U.S. Pat. No. 5,500,511, L for the selvaged susceptor of U.S. Pat. No. 5,508,496 should be less than W. With this selvaged susceptor, in the region immediately under the asymmetric induction work coil described in U.S. Pat. No. 5,444,220, current flows across the susceptor to the edges where the current density is lowest and the conductivity, highest.

Generally, the selvaged susceptor is somewhat wider than the bond line so that the selvage edge strips extend on either side of the bond line. Removal of the selvage edge strips after forming the weld leaves only a perforated susceptor foil in the weld. This foil has a relatively high open area fraction.

A structural susceptor allows Boeing to include fiber reinforcement within the weld resin to alleviate residual tensile strain otherwise present in an unreinforced weld. The susceptor includes alternating layers of thin film thermoplastic resin sheets and fiber reinforcement (usually woven fiberglass fiber) sandwiching the conventional metal susceptor that is embedded in the resin, and is described in greater detail in U.S. patent application Ser. No. 08/471,625. While the number of total plies in this structural susceptor is usually not critical, Boeing prefers to use at least two plies of fiber reinforcement on each side of the susceptor.

The structural susceptor permits gap filling between the welded composite laminates which tailors the thickness (number of plies) in the structural susceptor to fill the gaps, thereby eliminating costly profilometry of the faying surfaces and the inherent associated problem of resin depletion at the faying surfaces caused by machining the surfaces to have complementary contours. Standard manufacturing tolerances produce gaps as large as 0.120 inch, which is too wide to create a quality weld using the conventional susceptors.

Boeing can easily tailor the thickness of the structural susceptor to match the measured gap by scoring through the appropriate number of plies of resin and fiber reinforcement and peeling them off. In doing so, a resin rich layer will be on both faying surfaces and this layer should insure better performance from the weld.

To form a structural susceptor, Boeing takes a barbed susceptor and loosely bonds fiberglass reinforcing fiber and thermoplastic films in alternating layers symmetrically on both sides, similar to what is shown in U.S. patent application Ser. No. 08/471,625. The fiberglass reinforcement prevents the resin from fracture under the residual strain left after welding. Higher ductility resins such as PEEK, PEK, and ULTEM polyimide also resist fracture better than some thermoplastics. The thermoplastic films are preferably the same resin as that used to embed the metal foil and to fabricate the laminates. Sheet thicknesses for these films are usually about 0.001–0.002 inch (0.025–0.050 mm). The woven fibers are preferably oriented perpendicular and parallel to the longitudinal axis of the weld.

The structural susceptor is generally loosely bonded together by heat or pressure or both, but could be of essentially unitary construction if desired. Being loosely bonded helps in gap filling. Boeing uses at least two layers of fiber and thermoplastic on each side of the susceptor, but the absolute number is not critical. Boeing tested four different styles of fiberglass and achieved similar results with each, so the type or style of fiberglass does not seem to be critical.

The fiber suppresses cracking if the fiber volume is at least about 30%. The thermoplastic ensures a resin rich weld.

Described in greater detail in U.S. patent application Ser. No. 08/469,604, which we incorporate by reference, "smart" susceptors are magnetic alloys that have high magnetic permeability's but that also have their magnetic permeabilities fall to unity at their Curie temperature. At the Curie temperature, then, the susceptors become inefficient heaters. The alloys are selected to have Curie points close to the process temperature of welding and have low thermal expansion coefficients to match composites. The preferable alloys for this application are in a composition range of from 36% Ni to 44% Ni in Fe. Additional alloying elements such as Al, Cb and Ti allow these low expansion iron-nickel alloys to be age hardened and add to the cap/skin pulloff strength.

The need for a susceptor in the bond line poses many obstacles to the preparation of quality parts. The metal which is used because of its high susceptibility differs markedly in physical properties from the resin or fiber reinforcement, so dealing with it becomes a significant issue. A reinforced susceptor, which is described in U.S. patent application Ser. No. 08/469,986, overcomes problems with conventional susceptors by including delicate metal foils (0.10–0.20 inch wide×0.005–0.010 inch thick; preferably 0.10×0.007 inch) in tandem with the warp fibers of the woven reinforcement fabric. The woven arrangement holds the foils in place longitudinally in the fabric in electrical isolation from each other, yet substantially covering the entire width of the weld surface. This arrangement still allows adequate space for the flow and fusion of the thermoplastic resin. Furthermore, in the bond line, the resin can contact, wet, and bond with the reinforcing fiber rather than being presented with the resin-philic metal of the conventional systems. There will be a resin-fiber interface with only short runs of a resin-metal interface. The short runs are the length of the diameter of two weave fibers plus the spatial gap between the weave fibers, which is quite small. Thus, the metal is shielded within the fabric and a better bond results. In this woven arrangement the foil can assume readily the contour of the reinforcement. Finally, the arrangement permits efficient heat transfer from the foil to the resin in the spatial region where the bond will form.

Conventional susceptors are essentially planar (X-Y) metal sheets or laminates of planar films. Welds that embed these susceptors lack reinforcement in the Z-plane, but welds can include such reinforcement (with corresponding improvement in the pulloff strength) if they incorporate a barbed susceptor of U.S. patent application Ser. No. 08/486,560. A barbed susceptor typically uses a Fe—Ni alloy susceptor that is formed to include barbed, Z-pin reinforcement to provide improved pulloff strength. The alloy chosen for this susceptor has a coefficient of thermal expansion (CTE) that essentially matches the CTE of the composite and a Curie temperature of about 700° F. (370° C.), which is essentially ideal for thermoplastic welding of resins like KIIIA polyimide since it is slightly above the resin's melt temperature. For this application, an alloy of 42% Ni-58% Fe including $\gamma'$ strengthening elements of Al, Ti and Cb yields both low CTE and high strength. The susceptor is preferably made by laser cutting a foil of the material to form barbed tabs and pushing the cut tabs alternately up and down to give the susceptor a three dimensional character. Alternatively a woven wire mesh may be used in this application with alternating wires extending in the Z direction. The thermoplastic resin cures or consolidates around the barbs during the welding process which provides the pulloff strength improvement.

The barbed susceptor of U.S. patent application Ser. No. 08/486,560 usually is fabricated from an age-hardened Invar foil having a thickness of from 0.003–0.010 inch (0.075× 0.25 mm). It may be made from other materials having good electrical conductivity and high magnetic permeability. The susceptor may have a pattern of openings made by forming barbs in the Z-axis by folding prongs out of the X-Y plane. The result is a susceptor that resembles barbed wire. Each prong of the susceptor might also be barbed like a fishhook. Such barbs are readily formed simply by scoring the prong with a cut that starts relatively closer to the body of the susceptor and extends into the prong at an angle running from the surface toward the tip. This Invar susceptor is "smart", and helps to avoid excessive heating, because of its Curie point.

The barbed susceptor may also have a pattern of openings in the X-Y plane with uniform line widths of about 7 mils (0.18 mm) to define the peripheries of the diamond, as the other susceptors do, so that a fusion bond can occur through the susceptor. Of course, the openings can have shapes other than diamonds. The diamonds are easy to form by etching, stamping, or expanding and provide a convenient mechanism to control the longitudinal and transverse impedance, as described in Boeing's other patent applications. The diamonds can have L/W ratios less than or equal to 1.0 in the selvaged susceptor where Boeing was interested in influencing the eddy currents to run transversely into the solid edge strips. Other shapes can be used for the openings to create a foil that has a uniform impedance or whatever desired ratio in the longitudinal and transverse directions.

The barbed susceptor might be a "reinforced" multistrip susceptor similar to that described in U.S. patent application Ser. No. 08/469,986 with the strips being periodically cut to create Z-plane barbs. This multistrip concept may actually be best suited for resistance welding like that described in U.S. patent application Ser. No. 08/470,168 or heating in our induction solenoid coil heating workcell of U.S. Pat. No. 5,624,594 or 5,641,422, because these two processes induce currents that run longitudinally through the susceptor. The multistrip susceptor has low longitudinal impedance.

Welding researchers have devoted significant effort to develop inductor and susceptor systems to optimize the heating of the bond line in the welded thermoplastic assemblies. Another hurdle remaining to perfect the welding process to the point of practical utility for producing large scale aerospace-quality structures in a production environment is the aspect of the process dealing with the control of the surface contact of the faying surfaces. This aspect of thermoplastic welding controls the timing, intensity, and schedule of heat application. The material at the faying surfaces is brought to and maintained within the proper temperature range for the requisite amount of time for an adequate bond to form. Then, intimate contact is maintained while the melted or softened material hardens in its bonded condition.

Large scale parts, such as wing spars and ribs, and the wing skins that are bonded to the spars and ribs, are typically on the order of 20–30 feet long at present, and potentially, can be several hundred feet in length when the thermoplastic welding process is perfected for commercial transport aircraft. Parts of this magnitude are difficult to produce with perfect flatness. Instead, the typical part will have various combinations of surface deviations from perfect flatness, including large scale waviness in the direction of the major length dimension, twist about the longitudinal axis, dishing or sagging of "I" beam flanges, and small scale surface defects such as asperities and depressions. These irregularities interfere with full surface area contact between the faying surfaces of the two parts and can result in surface contact only at a few "high points" across the intended bond line. Additional surface contact can be achieved by applying pressure to the parts to force the faying surfaces into contact, but full intimate contact is difficult or impossible to achieve in this way. Applying heat to the interface by electrically heating the susceptor in connection with pressure on the parts flattens the irregularities when the resin melts. Additional time is needed after flattening to achieve full intimate contact. Extended use of heat and pressure may be excessive, however, and may result in deformation of the top part. When the overall temperature of the "I" beam flange is raised to the softening point, it will begin to yield or sag under the application of the pressure needed to achieve a good bond. If sagging occurs the necessary pressure will be lost and so will the final product configuration.

Boeing's multipass thermoplastic welding process described in U.S. Pat. No. 5,486,684 enables a moving coil welding process to produce continuous or nearly-continuous fusion bonds over the full area of the bond line to yield high strength welds reliably, repeatably, and with consistent quality. This process produces improved low cost, high strength composite assemblies of large scale parts, fusion bonded together with consistent quality. It applies heat according to a schedule that melts the resin at the faying surfaces yet maintains the overall temperature of the structure within the limit in which it retains its high strength. It avoids sagging and, so, does not require internal tooling to support the structure against sagging which otherwise could occur above the high strength temperature limit. The process also produces nearly complete bond line area fusion on standard production composite material parts having the usual surface imperfections and deviations from perfect flatness. The welding process eliminates fasteners and the expense of drilling holes, inspecting the holes and the fasteners, inspecting the fasteners after installation, sealing between the parts and around the fastener and the holes; reducing mismatch of materials; and arcing from the fasteners.

In the process, an induction coil is passed multiple times over a bond line while applying pressure at least in the region of the coil to the assembled components to be welded and maintaining the pressure until the resin hardens. The resin at the bond line is heated to the softening or melting temperature with each pass of the induction coil and pressure is exerted to flow the softened/melted resin in the bond line and to reduce the thickness of the bond line while improving the intimacy of the faying surface contact with each pass. Multiple passes then complete the continuity of the bond. The total time at the softened or melted condition of the thermoplastic in the faying surfaces is sufficient to attain deep inter diffusion of the polymer chains in the materials of the two faying surfaces throughout the entire length and area of the bond line. Doing so, produces a bond line of improved strength and integrity in the completed part. Because the total time of the faying surfaces at its softening temperature is separated into several segments, heat in the interface dissipates between passes so that each subsequent pass reheats the resin at the faying surfaces but does not raise the temperature of the entire structure to the degree at which it loses its strength and begins to sag. The desired shape and size of the final assembly is maintained.

Another moving coil welding operation seeks to apply a substantially constant and uniform pressure on the entire bond line throughout the welding operation. As described in U.S. patent application Ser. No. 08/367,557, such a welding operation, which Boeing calls "fluid tooling," includes an elongated vessel made of fluid impervious flexible material. The vessel has an elongated axis and an open end at each axial end of the vessel, and has a cross sectional dimension sized to accommodate the coil. Each axial end of the vessel is closed and sealed by an end closure. At least one of the end closures is removable for insertion of the coil into the vessel. A linear guide in the vessel extends axially for substantially the full length of the vessel and guides the coil for movement axially through the vessel. Power leads are connected to the coil and extend through a pass-through in one end closure to connect the coil to a source of high frequency electrical power to energize the coil to produce an alternating magnetic field. A motive system is provided for moving the coil axially along the vessel over the bond line at a controlled speed. The motive system generally includes a pair of magnets guided along opposite sides of the vessel and magnetically coupled to a ferromagnetic mass connected to the coil. The magnets are moved along their guides and pull the coil attached to the ferromagnetic mass inside the vessel. A backup structure exerts a downward force along the top of the vessel, pressurizing fluid sealed in the vessel and distributing the pressure uniformly over the top surface of the top part to press the top part against the bottom part and facilitate fusion bonding of the thermoplastic in the faying surfaces of the interface.

b. Fixed coil induction welding

Boeing has also experimented with thermoplastic welding using its induction heating workcell, and, of course, discovered that the process differs from the moving coil processes because of the coil design and resulting magnetic field. The fixed coil workcell presents promise for welding at faster cycle times than the moving coil processes because it can heat multiple susceptors simultaneously. The fixed coil can reduce operations to minutes where the moving coil takes hours. The keys to the process, however, are achieving controllable temperatures at the bond line in a reliable and reproducible process that assures quality welds of high bond strength. Boeing's fixed coil induces currents to flow in the susceptor differently from the moving coils and covers a larger area. Nevertheless, Boeing has developed processing parameters that permit welding with its induction heating workcell using a susceptor at the bond line. The fixed coil process is described in greater detail in U.S. Pat. No. 5,624,594, which we incorporate by reference.

Another advantage with the fixed coil process is that welding can occur using the same tooling and processing equipment used to consolidate the skin, thereby greatly reducing tooling costs. Finally, the fixed coil heats the entire bond line at one time to eliminate the need for shims that are currently used with the moving coil. Boeing can control the temperature and protect against overheating by using its "smart" susceptors as a retort or as the bond line susceptor material or both.

c. Temperature monitoring

In U.S. patent application Ser. No. 08/548,823 Boeing describes a system for thermoplastic welding to monitor the bond line temperature in real time allowing detection of the onset of flow of the thermoplastic resin. The system permits guidance control of the induction head to adjust its power, speed, or motion in response to the measured temperature. Basically, Boeing embeds at least one multinode thermocouple within the weld near the bond line in a layer adjacent the susceptor to measure the temperature under the moving coil.

The thermocouple is made by twisting the wires together or in a zig-zag fashion to form periodic nodes along the bond line. A single wire thermocouple configuration using constantan wire and using the copper susceptor as the second conductor also possible. The spacing of the nodes depend on the desired resolution, but, should be about 0.2 inch or so apart.

The thermocouple will be an open circuit prior to the onset of thermoplastic flow, and will not have a voltage output. At the onset of flow, the two thermocouple wires short and produce a thermoelectric voltage proportional to the temperature of the thermocouple junction. The thermocouple will read the temperature directly under the induction head, that being the hottest junction and also the one that is closest to the monitor input. The multinode thermocouple behaves like a series of parallel batteries. The node closest to the monitor produce the highest voltage amplitude because it directly in the hot zone. The same node also acts as a short to any other voltages produced by thermocouple nodes further away from the monitor. Each consecutive junction shorts the potential generated by the preceding node. If the node contact resistance is high there may be a small error.

As described in U.S. patent application Ser. No. 08/548, 823 Boeing welded a test panel with a sliding junction (multinode) thermocouple in the bond line. The thermocouple was made with two bare Chromel/aluminel, AWG #36 wires and wound in a zig-zag way on a piece of thermoplastic resin or was encapsulated with the resin. The thermocouple was located half way between the center of the bond line and the edge. Boeing also welded a second test panel with two multinode thermocouples near edges of the susceptor in the bond line. The thermocouples were located half way between the center and the edge on each side of the bond line, with nodes spaced one inch apart. The output of the two thermocouples tracked within 25° F.

By locating the thermocouples on the outer edges of the bond line, the voltages generated by the two thermocouples produce a guidance control function formed by combining the two thermocouple outputs with a differential amplifier bridge circuit. When the coil moves off center, it will produce uneven heating across the bond line. This heating will result in a differential thermocouple output signal used to restore the coil to the center of the susceptor, and, thereby, restore uniform heating across the bond line. Nevertheless, there also remains problems with the accuracy of positioning in the assembly, with shorting, and with reproducibility in what currently is a task requiring relatively high skill.

A drawback to this multinode thermocouple method of process monitoring and control for induction welding is that it is intrusive. The thermocouple wires remain in the bond line. The diameter of the thermocouple wires are as small as 0.001 inch. They should not present significant structural problems. The insulation of the thermocouple wire should be the same thermoplastic resin as that being welded and should not have any adverse effect on the structural properties of the bond.

In U.S. Pat. No. 5,573,613, Boeing also described a method for determining the susceptor temperature by measuring the change in impedance of the induction coil. As the susceptor heats, its electrical resistance changes as a function of the thermal coefficient of resistance (TCR) of the susceptor material, and that change is reflected back as a change in the drive coil impedance. An electrical circuit senses the varying impedance/resistance and converts that change into a change of temperature on a temperature display, or into a signal to adjust the power to the coil or the speed of travel of the coil along the bond line. The sensing circuit includes a high power bridge with a sensitive null arm to sense changes in the susceptor impedance due to temperature changes.

A simple L-R bridge detects the changing resistance of the susceptor as its temperature changes during inductive heating. The bridge includes a high-power transformer of about 500 watts operating at about 35–55 kHz connected across a pair of series-connected inductors $L_1$ and $L_2$ and a pair of series-connected resistors $R_1$ and $R_2$. Both series-connected pairs are connected to each other in parallel and in parallel with the transformer. A shunt with a voltage sensor (such as a voltmeter or an oscilloscope) is connected between the two resistors and the two inductors. The two sides of the bridge are asymmetric by at least 2:1 to put most of the power in the bond line for the sake of efficiency, since power dissipated in the reference side of the bridge is wasted. The two coils $L_1$ and $L_2$ are designed to track fairly closely so that their inductances and Q's (i.e. the dimensionless power ratio of stored to dissipated power) vary consistently with frequency. One of inductors $L_1$ or $L_2$ is the moving coil to transfer energy to the susceptor.

The bridge signal is used to control the welding process interactively by adjusting the power to the coil in a closed loop RF heating control circuit, or by adjusting the speed of travel of the coil over the bond line, or both, so as to maintain the melt pool temperature within the desired range of optimum processing temperature, that is, 620±25° F. in the case of the DuPont Avamid KIIIB polyimide. The signal is conditioned in a suitable conditioning circuit, which would depend on the voltage sensor used and could produce a digital signal to the power amplifier to turn the amplifier up or down, in the nature of a thermostat control, whenever the melt pool temperature drops below or exceeds the optimal temperature range. Preferably, the signal conditioner circuit produces a signal proportional to the voltage sensor signal to adjust the power to the work coil up or down from a predetermined average power level known to maintain a steady state temperature in the melt pool at the coil speed used. Nevertheless, overheating can still be a significant problem, especially if localized overheating arises from misalignment between the moving coil and the susceptor.

d. Steering the moving coil

A nonintrusive system associated with a moving induction coil, particularly one of the type described in U.S. Pat.

No. 5,313,037, self-steers the coil over the susceptor to avoid excessive, damaging overheating that otherwise might occur because of misalignment between the coil and the susceptor. Alternately, the system can sense the misalignment by the aberration in the magnetic field and can create a compensating "hot spot" with a differential, parasitic, secondary coil.

In U.S. patent application Ser. No. 08/565,566, when there is a misalignment between the primary coil of the induction head and the susceptor, the self-steering system produces a guiding command with a secondary coil to return the primary coil to the centerline. Alternately, the system can use a differential, parasitic secondary coil to compensate for the misalignment and to achieve better temperature uniformity in the bond line by adjusting the magnetic field. To accomplish these features, Boeing uses two, peripheral coils connected in differential mode to produce a null (i.e., no differential voltage) when the coil is centered over the susceptor. Doing so, Boeing tips the coils at 45° on the sides of the cup coil of U.S. Pat. No. 5,313,037.

A compensating secondary coil can be located in the centerline of the drive coil. This secondary coil has a "lazy 8" design and produces no measurable effect when inserted between the primary coil and the parts assembled for welding, unless the coil and susceptor are misaligned. When there is misalignment, the "lazy 8" forms a compensatory "hot spot" on the side of the susceptor that would otherwise be cool because of the misalignment. Compensation occurs provided that the "lazy 8" has a total resistance lower than the eddy, but the effect does not fully compensate for the offset.

Evaluating the quality and integrity of the thermoplastic weld

Turning now to FIG. 1, a thermoplastic welding head 10 that includes leading and trailing pneumatic pressure pads and a primary induction coil 25 disposed between the pads is supported on tooling headers 12 over thermoplastic composite parts to be fusion bonded together. The parts, in this example, include a thermoplastic spar 14 and a thermoplastic wing skin 16, only a small section of which is shown in FIG. 1. The spar 14 is in the form of an "I" beam having a top cap 18, a bottom cap 20, and a connecting web 22. The spar 14 extends lengthwise of the wing of the airplane for which the parts are being assembled, and the wing skin is bonded over the full length and surface area of the spar cap 18 with sufficient strength to resist the tensile and peeling forces the wing will experience in flight. The apparatus shown is more fully described in U.S. Pat. No. 5,556,565. The beams might be all composite construction or a hybrid metal webbed composite capped beam as described in U.S. Pat. No. 5,556,565. We could also join thermoset skins and spars with a hot melt thermoplastic adhesive.

Figure 7:
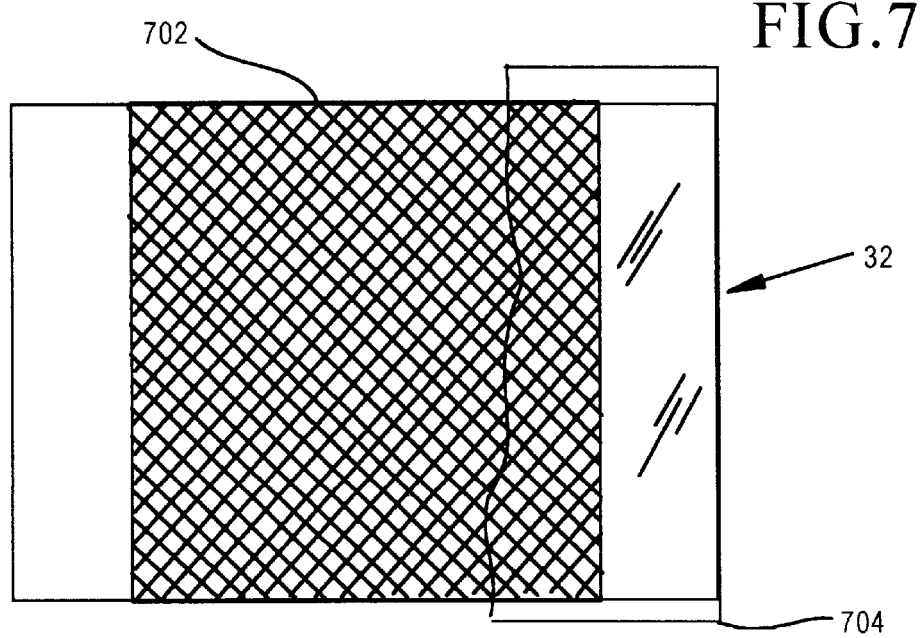
FIG. 7 is a schematic plan view of a typical susceptor tape.

A copper mesh susceptor 32 (i.e., a metal foil 702 susceptible to induction heating encapsulated in a thermoplastic resin 704, FIG. 7) is inserted between the spar cap 18 and the wing skin 16. Typically the encapsulating resin is the same or a slightly lower melting temperature formulation of the same thermoplastic resin of the spar cap 18 and the lower faying surface of the wing skin 16.

The welding head 10 can be any moving coil apparatus that is capable of applying pressure during induction heating of the bond line to promote fusion and after heating for a period sufficient for the resin to cool and harden in its bonded condition. Suitable welding heads are disclosed in U.S. Pat. Nos. 5,635,094; 5,444,220; and 5,313,037. A preferred welding apparatus includes an induction coil 25 for inducing eddy currents in the susceptor 32. The eddy currents heat the susceptor by electrical resistance heating and soften or melt the thermoplastic resin in the faying surfaces of the parts so it flows, interdiffuses, and fuses together with softened resin of the wing skin and spar cap upon cooling.

The coil shown in the '037 patent provides zero eddy current at the center with the current density increasing toward the edges. Use of a tailored susceptor is desirable to counterbalance the nonuniform eddy current density that the coil produces from centerline to edge to achieve uniform heating, and such a susceptor is disclosed in U.S. Pat. No. 5,500,511. A selvaged susceptor designed especially for use with the asymmetric induction coil of U.S. Pat. No. 5,444,220 is described in U.S. Pat. No. 5,508,496.

The primary induction coil 25 is mounted in the welding head 10 in the center of a lower frame which is pinned to a link connecting the lower frame to an upper frame. The upper frame is pulled by a motive apparatus including a stepper motor driving a drive sprocket and a chain loop through a reduction gear unit. A pair of camroll bearings projects from both sides of the lower frame into cam grooves milled into the inside surfaces of the headers to guide and support the lower frame. A similar set of camroll bearings projects outward from the upper frame into a straight cam groove to guide the upper frame as it is pulled by the chain loop from one end of the wing skin to the other.

The process of welding the wing skin to the spar cap begins with assembling the parts together with the susceptor 32 interposed between the faying surfaces of the parts. In the case of a wing box, we attach the susceptor 32 to the outer surfaces of the spar caps 18 and 20 and then sandwich the spars between the upper and lower wing skins 16. The parts are held in position and squeezed together by a force exerted by a pair of air bearing pads to which air under pressure is delivered by way of air lines and distributed to the air bearing pressure pads by separate air lines. The air to the pads reduces the frictional drag on the pressure pads on the top surface of the wing skin and helps to cool the parts after the coil has passed. The induction coil 25 moves along the intended bond line over the outer surface of the wing skin in general alignment ($\pm 0.125$ in) with the susceptors while producing an alternating magnetic field which projects through the wing skins and around the susceptor, generating eddy currents in the susceptor. The eddy currents induced by the magnetic field are of sufficient amperage to heat the susceptor, raising the temperature of the thermoplastic material in the faying surfaces to its softening or melting temperature. After the first pass of the welding head over each bond line to seal the box, the process is repeated three or more times, usually increasing the power to the coil after the second pass and, if desired, increasing the pressure exerted by air cylinders on the pressure pads.

The bond strength improves with multiple passes of the welding head over the same bond line. Multiple passes of the induction coil serves to create the optimal conditions for achieving a fusion bond with the desired characteristics of continuity over the entire bond line, and substantial molecular interdiffusion of the materials in the faying surfaces to produce a bond line of high pulloff strength with the complete or nearly complete absence of voids, as discussed in U.S. Pat. No. 5,486,684. Welds having higher pulloff strengths use a barbed susceptor of U.S. patent application Ser. No. 08/486,560 on the bond line.

The mechanisms for achieving a fusion bond include intimate contact and "healing." Intimate contact of the two faying surfaces is a function of force exerted on the parts to squeeze them together, and temperature-dependent viscosity. The force exerted on the parts is distributed over a certain surface area as interfacial pressure tending to bring the faying surfaces together. The viscosity of the surface material is manifested by the tendency of high spots in the surface to yield of flow so that low spots in the two surfaces can come together. "Healing" is partly a process in which molten or softened materials flow together and blend where they come into contact, and partly a process of molecular penetration of the polymer chains in the material of one surface into the molecular matrix of the material in the other faying surface. The average penetration distance of the polymer chains, without the beneficial mixing effect achieved by flowing the materials in the faying surfaces, increases as a quarter power of time (i.e., $t^{0.25}$).

Objective and easily made observations of a bond line that are indicative of "healing" of the quality of the bond are reduction in bond line thickness, improved ratio of bonded to unbonded surface area in the bond line (or expressed conversely, a reduction of the amount of unbonded surface area in the bond line), and improved pass-through of a bonding resin through openings in the susceptor.

Irregularities, such as hollows, depressions, and asperities (i.e., peaks) in the faying surfaces of the parts, and other deviations from perfect flatness can interfere with and prevent continuous intimate contact along the full surfaces of the parts where bonding is intended. These deviations from perfect flatness include small scale surface features such as asperities, depressions or hollows, scratches and bumps, and also large scale features such as waviness in the direction of the major length dimension, twist about the longitudinal axis, dishing or sagging of "I" beam flanges, and warping such as humping or bowing in the longitudinal direction. The structural susceptor is particularly suited for dealing with these problems.

Boeing's goal is to produce aircraft structure that eliminates fasteners. Welded structure will be far less expensive because welding eliminates the labor to drill holes accurately and to inspect the fasteners after installation. We also will avoid other problems that fasteners introduce, such as sealing around the fastener and the holes, mismatch of materials, and arcing from the fasteners. To replace the fasteners, however, requires confidence that the welds are uniform and consistent. A failure at any weak point in the weld could lead to catastrophic unzipping of the entire welded structure. One of the most important problems with quality welding is temperature uniformity along the bond line to achieve uniform and complete melt and cure of the resin. Being a "smart" susceptor, our barbed susceptor has a Curie temperature slightly higher than the welding temperature (i.e., about 700° F.) so the possibility of disastrous overheating is reduced. The present invention is a reliable method to test the weld quality able to distinguish low strength, inadequate bonds from well bonded welds.

Boeing embeds the foil in the resin to simplify the welding process. Making a foil/resin tape eliminates the steps of applying separate layers of resin between the respective elements in a composite-susceptor-composite assembly. It also ensures that there will always be adequate resin proximate the susceptor and essentially uniform resin thickness across the welding bond line. The typical tape is about 2–4 inches wide with KIIIA Avimid resin (an aromatic polyimide), although the resin can be PEEK, PEKK, PES, PEK, ULTEM, or any other thermoplastic. The resin must be compatible with the matrix resin in the composite and generally is the same resin as the matrix resin when welding thermoplastic composites. For the "welding" analog for thermoset composites, the resin will likely be a comparable thermoplastic formulation of the matrix resin in the composites or a compatible resin.

Figure 2:
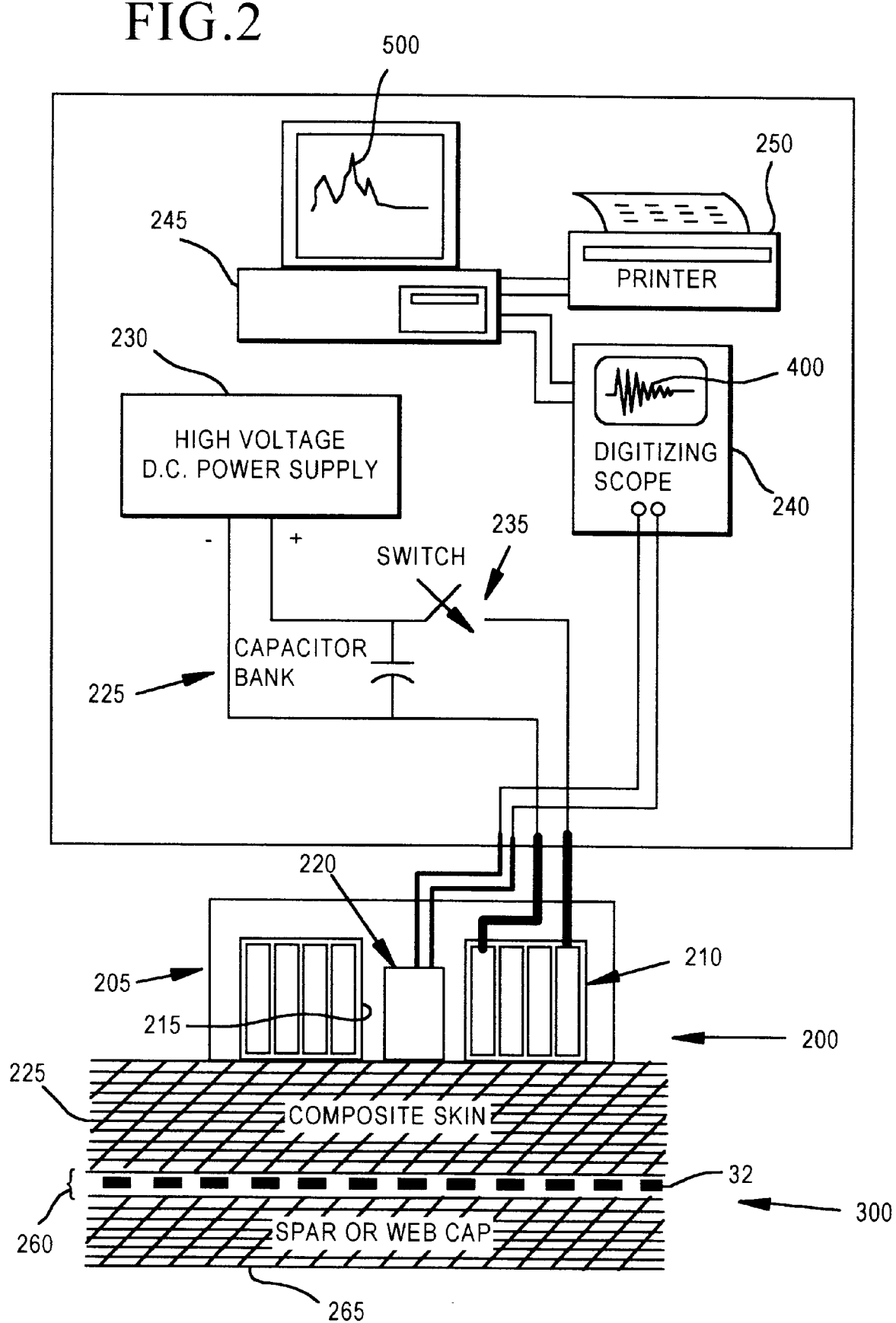
FIG. 2 is a schematic view, partially in section, illustrating a cup coil for inducing vibrations in the susceptor of thermoplastic welds.

As shown in FIG. 2, the transmitter-receiver 200 of the present invention is similar in overall design to the cup coil of U.S. Pat. No. 5,313,037. The transmitter-receiver, nonetheless, is adapted for the nondestructive evaluation (NDE) method of the present invention to produce an electromagnetic pulse to vibrate the susceptor and to receive the returning acoustic signal representing the susceptor vibration. The transmitter-receiver 200 has a housing 205 which contains the cup (pancake) coil 210 similar to that described in U.S. Pat. No. 5,313,037 around a central pole 215. Unlike the patented cup coil, however, our probe head carries a shielded acoustic emission transducer (receiver) 220 at the center of the pole 215 or adjacent to the coil 210 (for a better signal-to-noise ratio). The transmitter-receiver 200 may also include active cooling plumbing for circulating cooling water or other suitable coolant around the pancake coil 210 during its operation, analogous to the cooling circuit for Boeing's induction coil. We generally do not include this cooling plumbing.

FIG. 2 also illustrates that the pancake coil 210 is connected to a 240 $\mu$F capacitor bank 225 and high voltage D.C. power supply 230 so that an electromagnetic pulse of predetermined characteristics (i.e., time, energy, frequency, and amplitude) can be introduced to the coil 210 by activating the switch 235. The power supply typically supplies power in the range from 0–10 kV, and we prefer 500 V. The pulse to the coil has the characteristics generally shown in FIG. 4 with a duration of about 0–10 msec at 500±0.1–5.0 V.

The receiver circuitry is also shown in FIG. 2, and includes a digitizing oscilloscope 240 connected to the acoustic emission receiver 220 for viewing the acoustic signal representing the susceptor vibration; a computer processor 245 for transforming the acoustic signal from the time domain to the frequency domain or to provide other suitable signal processing to allow discrimination of the weld quality; and a printer 250 for plotting the various evaluation results. The sensitivity of the receiver is a function of the pulse current, the distance through the composite to the susceptor, the thickness of the composite, and the conductivity of the susceptor and composite. The current and distance are factors because they represent the strength of the induced magnetic field reaching the susceptor. The composite thickness is a factor because the returning acoustic signal must travel through the composite. The conductivities are also related to the magnetic field strength at the susceptor. We have not discovered any differences in performance because of the use of different resins in the composite or the bond.

As shown in FIG. 2, the transmitter-receiver 200 is positioned over the welded assembly 300 (such as a composite skin to composite spar weld) to pulse the susceptor 32 and to receive the resulting acoustic signal that the vibrating susceptor creates. The acoustic emission receiver 220 is generally located above the centerline of the susceptor 32 inside (substantially concentric with) or outside the windings of a pancake coil 210. The AE receiver might also be located on the opposite face of the assembly if access to both sides of the assembly is possible. In most of our tests we used this alternate "through assembly" arrangement, but we prefer the transmitter-receiver arrangement shown in FIG. 2 for assessing authentic aerospace structure where blindside access generally is impractical or unavailable. An EM pulse from the pancake coil 210 penetrates through the composite skin 255 and into the weld 260 where it induces eddy currents in the susceptor 32. The pulse may involve the lower composite spar or web cap 265 without significant interaction with the composite.

To conduct a test, we step the transmitter-receiver incrementally along the bond line limited only by the time required to recharge the capacitor bank, which is quite fast. For an automated inspection, we would couple the transmitter-receiver to a stepper motor or other suitable motive means to convey the transmitter-receiver incrementally over the bond line. At each pulse, the transmitter-receiver is stationary.

We believe that our test method should work with continuous or segmented susceptors and with dispersed microparticles at the bond line, although our tests have focused on narrow (2–3 inch) and wide (4–5 inch) copper susceptors having an expanded diamond pattern or etched square pattern of openings, like those described in Boeing's patents. We have not tested a bond line reinforced with Z-pins, but we expect our method to work there as well. The Z-pins may alter the characteristic return signal, however, by modulating the susceptor's vibrational modes.

Figure 3:
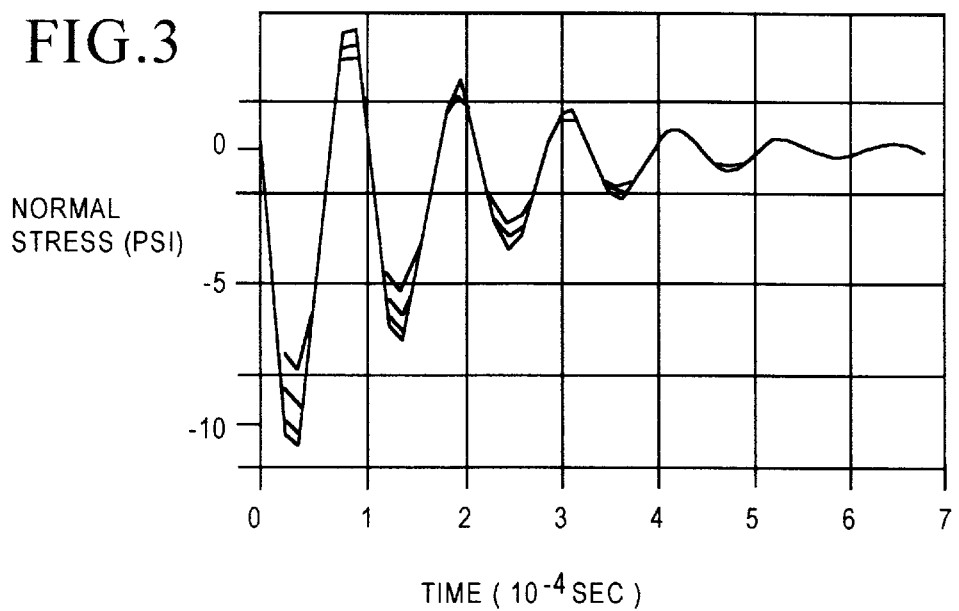
FIG. 3 is a graph showing the normal stresses induced in a susceptor embedded in a thermoplastic weld by EM pulses from the coil of FIG. 2.
Figure 4:
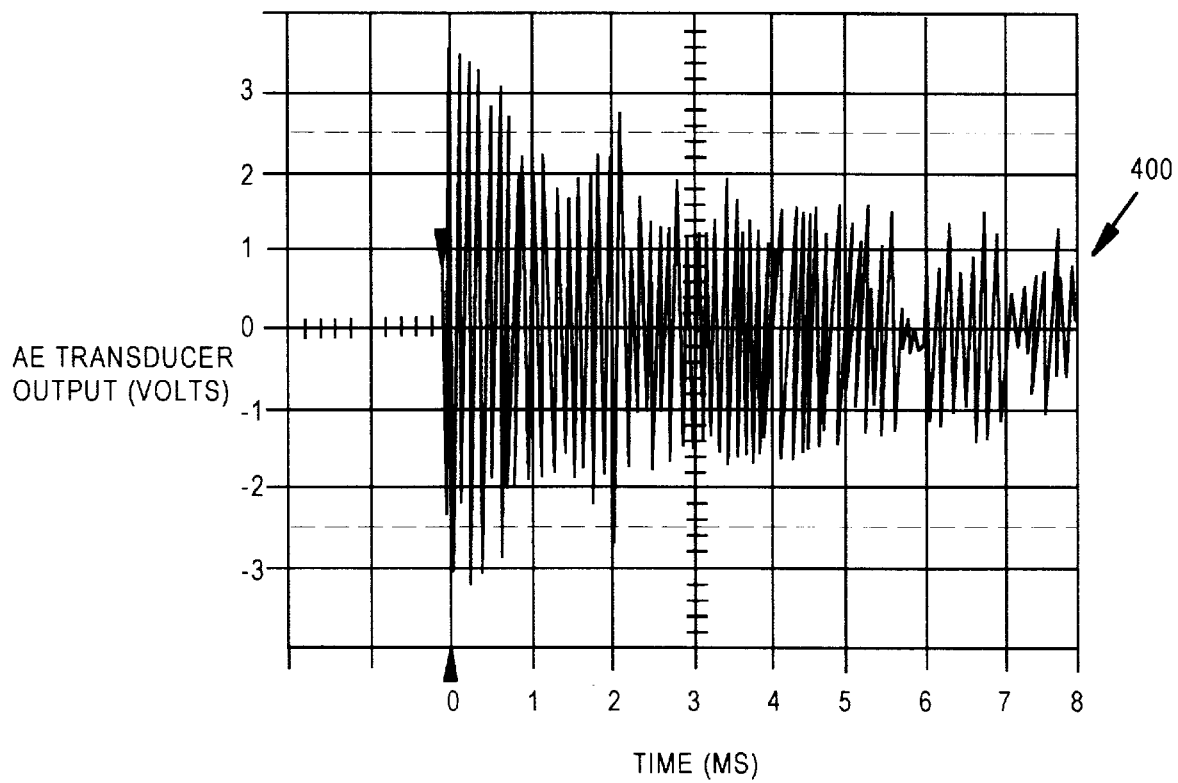
FIG. 4 is a schematic graphical representation of the acoustic signal created by pulsing a susceptor in a well bonded thermoplastic weld.
Figure 5:
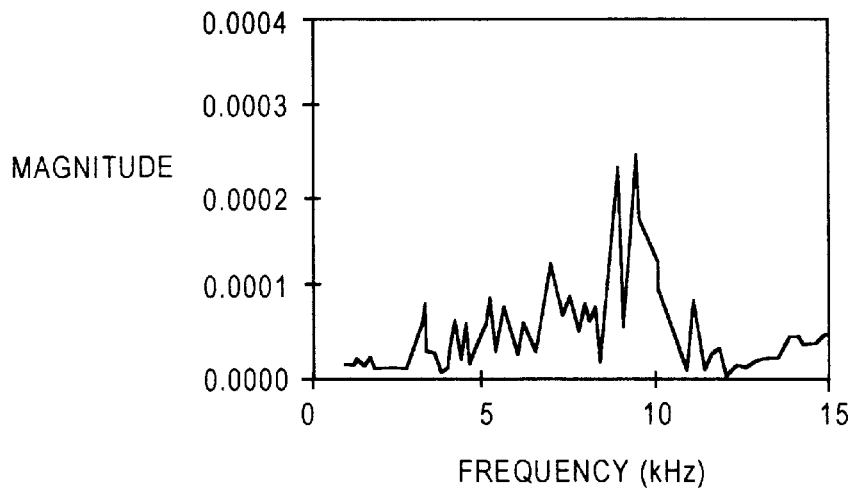
FIG. 5 is a graphical representation of the acoustic signal created by pulsing a susceptor in an adequate strength, good quality thermoplastic weld.
Figure 6:
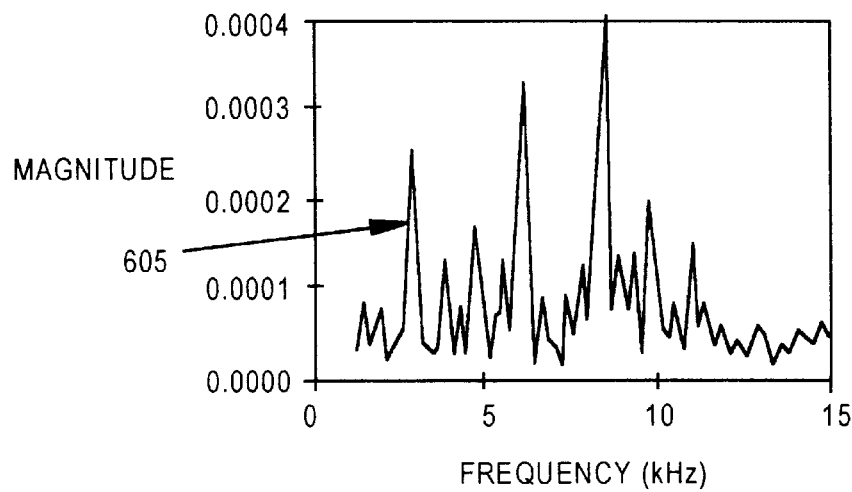
FIG. 6 is a graphical representation of the acoustic signal created by pulsing a susceptor in a low strength, poor quality thermoplastic weld.

When pulsed, the susceptor 32 experiences stresses that translate into an acoustic signal 400 representative of the susceptor vibration that results because of the stresses. FIG. 3 shows the theoretical stress on the susceptor created by a 20 mV, 15.6 kAmp pulse of about 0.0001 sec duration. This stress produces an acoustic signal from the compression and tension of the weld resin that propagates through the assembly's composites to the AE receiver 220. FIG. 4 shows a typical analog acoustic signal in the time domain (i.e., amplitude v. time), which we transform the acoustic return signal using a suitable Fourier transform algorithm or other suitable transform to the frequency domain (i.e., amplitude v. frequency). Our signal processing is applicable to analog or digital representations of the acoustic vibration, although analog processing probably is simpler. In the frequency domain 500, we are able to discriminate between welds of adequate strength and those of dangerously low or no strength. In particular, FIG. 5 shows the typical spectral response for a weld having adequate strength while FIG. 6 shows the spectral response for a weld having inadequate strength. The significant characteristic in the spectral response between an adequate weld and an inadequate, low strength weld is the presence of low frequency peaks 605 in the spectral response in the 1–3 kHz range for the inadequate welds. The precise location of this low frequency signal depends upon the geometry of the part under test and the susceptor, but, for all configurations, we have been able to distinguish quality welds from low strength welds or bonds by finding this low frequency peak in the return of the low strength bonds.

Figure 8:
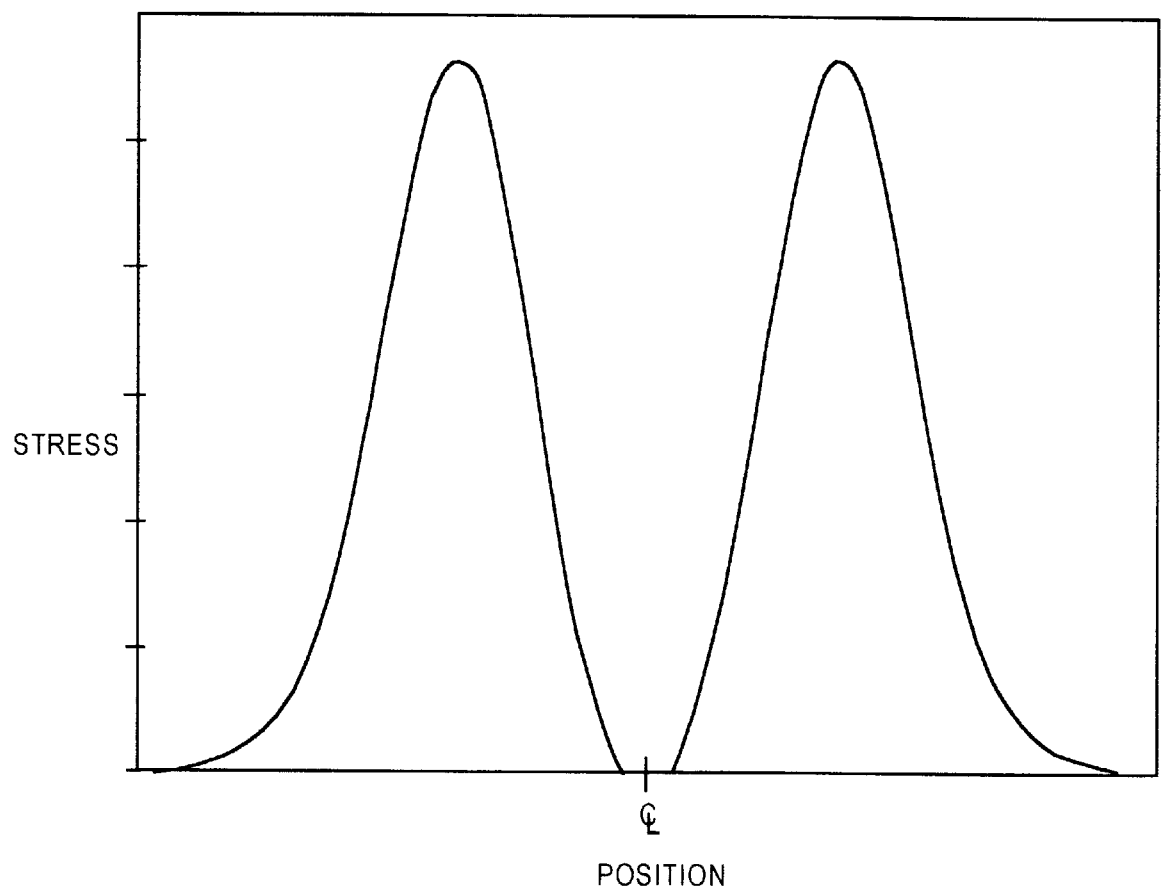
FIG. 8 is a schematic representation of the maximum stress on the susceptor as a function of position from the centerline of the coil assuming there is no offset between the coil and susceptor.
Figure 9A:
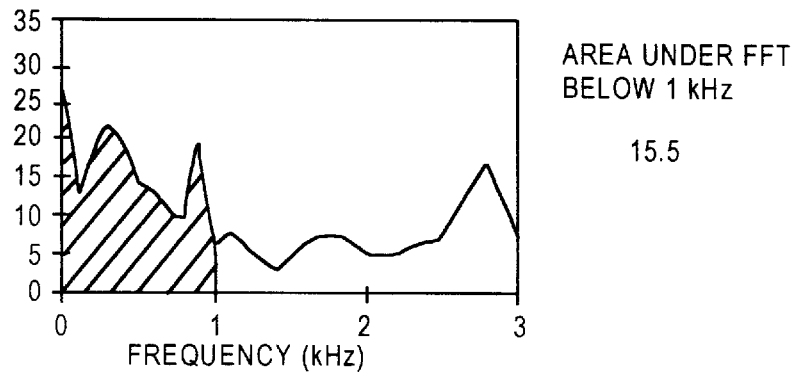
FIGS. 9 A–D are graphs showing the typical correlation between bond strength and the area under the frequency domain Fourier Transform curve for a low frequency response for a narrow susceptor.
Figure 9B:
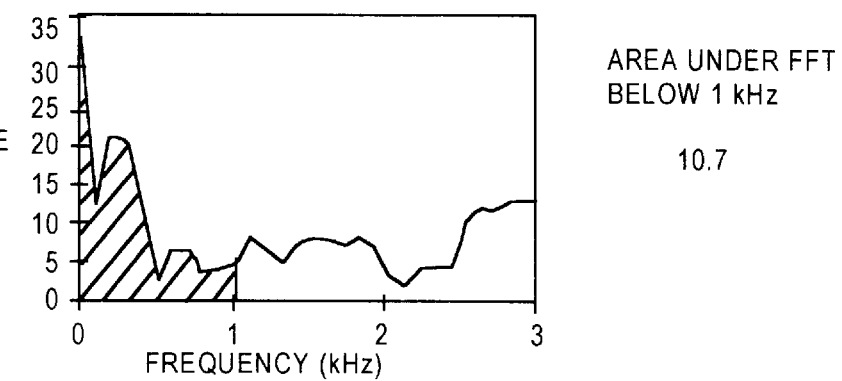
Figure 9C:
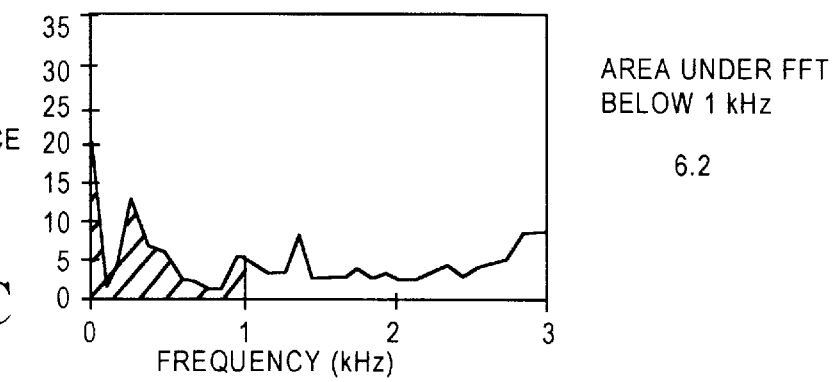
Figure 9D:
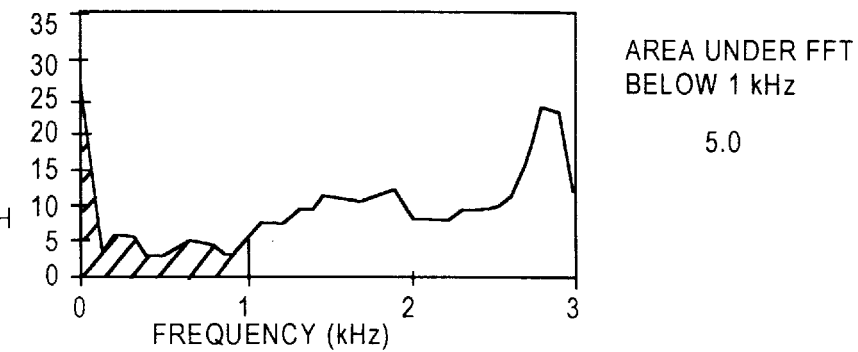

FIG. 8 shows the relationship of stress in the susceptor as a function of position displaced from the centerline when a pulse is transmitted with our pancake coil transmitter and the return signal is received at the center of the coil. The stress is bimodal and is symmetrical about the central pole of the coil and centerline of the susceptor. That is, $\delta=0$.

Alignment between the transmitter-receiver and susceptor does not appear to be a critical concern, which makes our method easier to use. We achieve the best results, however, when the receiver is about 1 inch laterally from the transmitter. The vibrating susceptor creates a dispersive, global acoustic signal in the composite. The pulse, being so short in duration, apparently does not heat the susceptor or bond line significantly.

Figure 10:
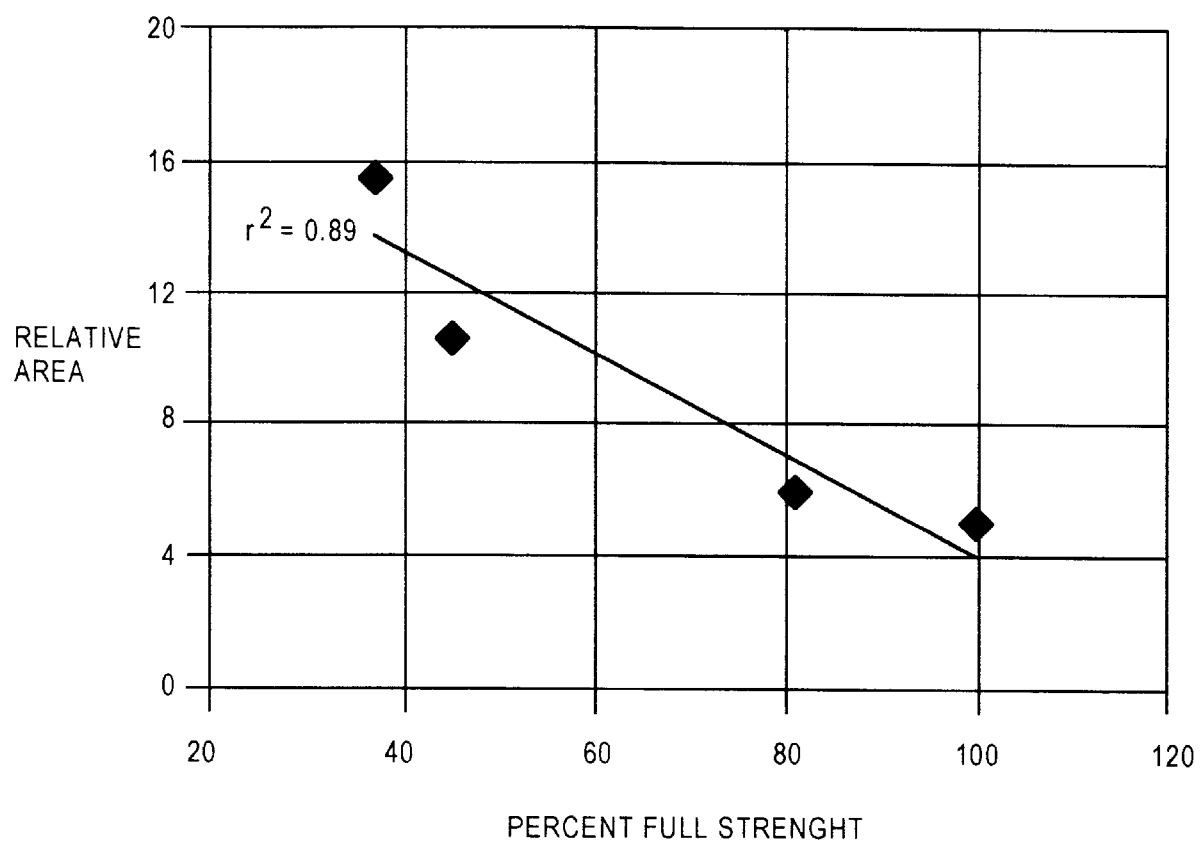
FIG. 10 is a graph showing relative bond strength as a function of the area under the low frequency response curve.

The area under the vibration signal curve for frequencies up to 1 kHz provides a convenient correlation for the strength of the bond. The bond strength is inversely proportional to the area. FIGS. 9A–D show bonds of four different strengths, the frequency response curve up to 1 kHz, and the area under the frequency response curve. The correlation for a narrow susceptor I-beam weld. Values of strength are normalized relative to a reference strength and the normalized plot of FIG. 10 shows a substantially linear degradation of relative bond strength as the area under the response curve increases.

Narrow susceptors exhibit essentially Mode 1 vibrations. Wider susceptors may vibrate differently, so the bond strength v. area correlation may not hold for wider susceptors.

While we have described preferred embodiments, those skilled in the art will readily recognize alterations, variations, and modifications which might be made without departing from the inventive concept. Therefore, interpret the claims liberally with the support of the full range of equivalents known to those of ordinary skill based upon this description. The examples are given to illustrate the invention and not intended to limit it. Accordingly, limit the claims only as necessary in view of the pertinent prior art.

We claim:

1. A nondestructive method for evaluating the integrity and strength of a thermoplastic weld or adhesive bond having an embedded susceptor, comprising the steps of:

(a) transmitting an electromagnetic pulse in the form of an oscillating magnetic field from an induction coil positioned near one surface of a composite assembly containing the weld or bond, the pulse traveling through the weld or bond to the susceptor, the pulse being received by the susceptor to cause the susceptor to vibrate at ultrasonic frequency and to create an acoustic signal representative of ultrasonic vibrations in the susceptor;

(b) receiving at the one surface of the composite assembly the acoustic signal representing the ultrasonic vibration of the susceptor transmitted through the weld or bond; and (c) analyzing the received signal to assess the thermoplastic weld quality or adhesive bond quality in terms of integrity and strength.

2. The method of claim 1 wherein the step of analyzing includes transforming the signal to the frequency domain and discriminating low strength bonds by the presence of low frequency vibrations.

3. A nondestructive method for evaluating the quality of a bond between two elements in a bonded composite assembly, comprising the steps of:

(a) inducing vibrations with an oscillating magnetic field transmitted through the composite assembly and through the bond for reception in a metal mesh susceptor embedded within the bond, the vibrations of the susceptor creating an acoustic signal;

(b) receiving the acoustic signal as the signal emerges from one surface of the composite assembly; and (c) analyzing the signal to deduce the quality of the bond in terms of integrity and strength.

4. A system for evaluating the integrity and strength of a thermoplastic weld or adhesive bond having an embedded susceptor, comprising:

(a) an electromagnetic pulse generator to generate pulses to vibrate the susceptor;

(b) a receiver for receiving an acoustic signal generated by the vibrating susceptor; and (c) an analyzer for discriminating the strength of the weld or bond from the acoustic signal.

5. An acoustic signal stored in analog or digital form on suitable recording media, the signal representing the vibration of an embedded susceptor in a thermoplastic weld or adhesive bond arising from pulsing the susceptor inductively with an electromagnetic pulse test signal.

6. A method for nondestructively determining that a structural bond being a thermoplastic weld or a structural adhesive bond between elements in a composite assembly has adequate strength, the weld or bond including an embedded susceptor and joining at least two composites, the method comprising the step of:

(a) inducing vibration in the susceptor inductively by inputting an electromagnetic test pulse through the assembly for reception by the susceptor to produce acoustic vibrations detectable at a surface of one composite;

(b) detecting the acoustic vibrations from the susceptor when the vibrations emerge from the assembly; and (c) identifying that the detected acoustic vibrations lack low frequency acoustic vibrations indicative of low strength structural bonds in the 1–3 kHz range.

7. The method of claim 3 wherein the susceptor is in a thermoplastic weld joining a wingskin and a spar.

8. The method of claim 1 wherein the pulse has a duration of up to 10 msec at about 500V.

9. The method of claim 3 wherein the pulse has a duration of up to 10 msec at about 500V.

10. The method of claim 6 wherein the pulse has a duration of up to 10 msec at about 500V.

* * * * *